United States Patent
Cox et al.

[11] Patent Number: 5,902,565
[45] Date of Patent: *May 11, 1999

[54] SPRAY DRIED VACCINE PREPARATION COMPRISING ALUMINIUM ADSORBED IMMUNOGENS

[75] Inventors: John Cooper Cox, Bullengarook, Australia; Robert Edward Sparks, Kirkwood, Mo.; Irwin Clay Jacobs, Eureka, Mo.; Norbert Simon Mason, St. Louis, Mo.

[73] Assignee: CSL Limited, Parkville, Australia

[ * ] Notice: This patent issued on a continued prosecution application filed under 37 CFR 1.53(d), and is subject to the twenty year patent term provisions of 35 U.S.C. 154(a)(2).

[21] Appl. No.: 08/481,403
[22] PCT Filed: Dec. 24, 1993
[86] PCT No.: PCT/AU93/00677
§ 371 Date: Jul. 10, 1995
§ 102(e) Date: Jul. 10, 1995
[87] PCT Pub. No.: WO94/15636
PCT Pub. Date: Jul. 21, 1994

Related U.S. Application Data

[63] Continuation-in-part of application No. 08/002,485, filed as application No. PCT/AU93/00677, Feb. 24, 1993, abandoned.

[51] Int. Cl.$^6$ ............ A61K 51/00; A61K 9/16; A61K 9/50; A61K 9/60
[52] U.S. Cl. ............ 424/1.29; 424/1.33; 424/489; 424/499; 424/457; 424/460; 424/461
[58] Field of Search ............ 424/489, 457, 424/460, 461, 1.29, 1.33, 499

[56] References Cited

U.S. PATENT DOCUMENTS

| | | | |
|---|---|---|---|
| 4,578,270 | 3/1986 | Csizer et al. | 424/92 |
| 4,806,350 | 2/1989 | Gerber | 424/88 |
| 5,242,686 | 9/1993 | Chu et al. | 424/92 |

FOREIGN PATENT DOCUMENTS

| | | |
|---|---|---|
| 79929/87 | 10/1987 | Australia . |
| 33433/89 | 3/1989 | Australia . |
| 29557/89 | 8/1989 | Australia . |
| 41876/89 | 3/1990 | Australia . |
| 0 486 959 | 11/1991 | European Pat. Off. . |
| 645270 | 9/1984 | Switzerland . |
| 1567503 | 10/1980 | United Kingdom . |

OTHER PUBLICATIONS

Eldridge et al, Infection and Immunity, Sep. 1991, pp. 2978–2986 vol. 59, No. 9.

Bodmeier et al, J Pharm. Pharmacol. 1988 vol. 40, pp. 754–757.

Singhi et al, Pharmaceutical Research, vol. 8, No. 7, 1991 pp. 958–961.

Primary Examiner—Lila Feisee
Assistant Examiner—Geetha P. Bansal
Attorney, Agent, or Firm—Jacobson, Price, Holman & Stern, PLLC

[57] ABSTRACT

Vaccine preparations in stable particulate form are disclosed. An immediate-release preparation comprises an immunogen adsorbed to an aluminum adjuvant. A controlled- or delayed-release preparation comprises microspherical particles comprising a continuous matrix of biodegradable polymer containing discrete, immunogen-containing regions.

26 Claims, No Drawings

SPRAY DRIED VACCINE PREPARATION COMPRISING ALUMINIUM ADSORBED IMMUNOGENS

This application is a continuation of Ser. No. 08/002,485, filed Jan. 8, 1993 (abandoned), and a 371 of PCT/AU93/00677 filed Dec. 24, 1993.

FIELD OF THE INVENTION

This invention relates to vaccine preparations, and in one particular embodiment it relates to vaccine preparations of the type which are variously described as controlled- or delayed-release vaccines, pulsatile or pulsed-release vaccines and single-shot vaccines. The preparations of the present invention are relevant for use as human and veterinary vaccines, and are provided in the form of a dry powder, which can be subsequently incorporated into a liquid suspension or in a solid pellet or implant for administration. Typically, administration of the vaccine preparation of the present invention in the form of a liquid suspension is by parenteral administration, for example by subcutaneous or intramuscular injection.

BACKGROUND TO THE INVENTION

Delivery of a full course of vaccine in a single dose has held attraction in both human and veterinary medicine and a number of patents and other publications (e.g. U.K. Patent No. 1,567,503) have addressed this possibility. For veterinary applications, the advantages include:

(i) reduced time—animals need be handled only once, (ii) reduced cost—single veterinary visit and reduced handling costs, (iii) guaranteed compliance with recommended dose schedule (number of doses, time interval between doses).

In human medicine, the above three advantages are also important with compliance being extremely important in developing countries where repeated access to infants is often not possible. In addition, the pain and suffering associated with vaccination, especially of infants, is an additional reason to favour a single-dose vaccine in human medicine.

Early studies of vaccination using inactivated vaccines (generally tetanus or diphtheria toxoids), have demonstrated the importance of two or more discrete doses of vaccine with an interval of at least 4 weeks, and preferably longer, between doses. A third dose is sometimes necessary to induce an adequate immune response, especially in young animals or infants where transfer of maternal antibodies could interfere with the preliminary immune response.

Recent studies in theoretical immunology have supported these findings and introduced the phrase "affinity maturation". Affinity maturation describes the process whereby plasma cells secreting high affinity antibodies to the desired immunogen are preferentially selected whilst plasma cells secreting antibody of lower affinity are lost. The process involves competition between follicular dendritic cells and plasma cells for antigen binding and thus can only occur effectively in the presence of limiting amounts of antigen. The process of affinity maturation may not commence until 2 to 3 weeks after a primary vaccine dose and it is important that the second dose of antigen not be given until the process is effectively complete. This is readily achievable in a multidose vaccination schedule provided the first dose does not contain too much antigen. However, for this process to be achieved in a single dose delayed-release vaccine, it is important that the second and subsequent doses do not release their antigen payload prematurely. To achieve this, the antigen must be contained within a matrix which has a defined time of degradation. This matrix should be biodegradable, although biocompatible matrixes have been proposed as acceptable. A number of options have been reviewed by Cox & Coulter, 1992.

The major effort to develop delayed release vaccines has centred round the studies of Eldridge et al., 1990; 1991, who used the biodegradable copolymer—polylactide coglycolide to produce antigen-containing microspheres and observed a delayed-release of the antigen contents in vivo (see also Australian Patent Specifications Nos. 79929/87 and 33433/89). Similar observations have been reported by Kreuter, 1990 using nanoparticles produced from acrylate polymers. Although the above workers were able to show that the concept of delayed-release vaccines was possible, the process they used in the preparation of the vaccines suffered from a number of deficiencies making it unsuitable for the routine manufacture of a vaccine. The major problems were:

(i) exposure of biological materials to denaturing chemical and physical conditions, and (ii) difficulty of scale-up, (iii) low efficiency of incorporation of hydrophilic compounds (e.g. proteins).

In European patent publication No. 0486959, in the name of Vectorpharma International SpA, there are disclosed controlled release, particulate pharmaceutical compositions containing pharmacologically active substances, the compositions comprising a biodegradable polymer such as polylactic acid, polyglycolic acid and copolymers thereof and/or other polymers including a polysaccharide gellifying and/or bioadhesive polymer, an amphiphilic polymer, an agent modifying the interface properties of the particles and the pharmacologically active substance. In the preparation of the pharmaceutical composition, the polymeric substituents are co-solubilised with the agent modifying the interface properties either in the absence of any solvent or in the minimum necessary amount of solvent, and the pharmacologically active substances then dissolved or dispersed in the polymer solution prior to formation of the final particles, for example by emulsion, extrusion, spray drying or spray-congealing techniques. As previously described, this technique suffers from a major disadvantage in that the pharmacologically active substance is directly exposed to the mixture of polymeric compounds together with any solvents therein, which results in the denaturing of biological materials used as the pharmacologically active substance.

It is a principal object of the present invention to provide a vaccine preparation and method for the production thereof wherein the immunogenic material is not exposed to an organic solvent or other organic phase when in soluble form, so as to ensure that there are no conformational changes in the immunogen, in other words to maintain the native structure of the immunogen.

SUMMARY OF THE INVENTION

In accordance with a first aspect of the present invention, there is provided an immediate-release vaccine preparation in stable, dry particulate form, said particles being microspherical particles prepared by spray-drying, comprising an inmmunogen adsorbed to an aluminium salt adjuvant.

In accordance with this aspect of the invention, there is also provided a method for the production of an immediate-release vaccine preparation in stable, dry particulate form as described above, which comprises the steps of forming an aqueous suspension of aluminium salt-adsorbed immunogen, and subsequently spray-drying said suspension.

Freeze-drying or lyophilisation of similar preparations has been described by Csizer et al. (U.S. Pat. No. 4,578,270). This process has a number of shortcomings, most importantly the need to add large amounts of both dextran and protein so that partial retention of the aluminium gel structure can be achieved (40 and 6–4 mg/ml respectively). This large addition of protein can act to displace vaccine antigens from the aluminium gel and in addition would, in most cases, be immunogenic and as a result tend to swamp the immune response to the vaccine antigen. Other problems associated with lyophilisation are that it is less amenable to large-scale production, equipment costs are significantly higher and the resultant product tends to form flakes rather than free-flowing microgranules.

Surprisingly, the gel-forming nature of aluminium gels is completely retained during spray-drying even in the absence of any other materials (apart from minimal quantities of vaccine antigen, typically 1 to 10 $\mu$g/ml) which could exert a stabilising effect. Addition of water to the spray-dried powder results in the instant formation of a typical gel, with sedimentation properties similar to the starting material.

In accordance with a second aspect of the present invention, there is provided a controlled or delayed-release vaccine preparation in stable, dry particulate form, said particles being microspherical particles prepared by spray-drying comprising a continuous matrix of biodegradable polymer containing one or more discrete, immunogen-containing regions.

In this aspect, the invention also provides a method for the production of a controlled- or delayed-release vaccine preparation in stable, dry particulate form as described above, which comprises the steps of forming an emulsion of an aqueous suspension comprising the imnunogen and optionally an adjuvant in a continuous organic phase having said biodegradable polymer dissolved therein, and subsequently spray-drying the water-in-oil emulsion to form said microspherical particles which comprise a continuous matrix of polymer containing discrete, immunogen-containing regions.

In an alternative method, these microspherical particles are produced by spray-drying a suspension of a particulate immunogen-containing material, preferably an immediate-release vaccine preparation in stable particulate form as broadly described above, and optionally an adjuvant in a continuous organic phase having said biodegradable polymer dissolved therein, to form said microspherical particles comprising a continuous matrix of polymer containing discrete, immunogen-containing regions.

These two processes confer major advantages over methods described previously, e.g. Eldridge et al. 1991, O'Hagan et al. 1991, Singh et al. 1991 and Bodmeier & Cheng 1988. In the processes of Eldridge et al. 1991 and Bodmeier & Chen 1988, proteins are directly exposed to the organic solvents required to dissolve the PLG. As a result, antigens are denatured and, because most antigens are water-soluble, poor efficiencies of incorporation result. O'Hagan et al. 1991 and Singh et al. 1991 devised complex processes to try to overcome these deficiencies. Neither process was amenable to commercial scale, and in addition the former showed poor efficiency of incorporation whilst the latter necessitated injection of large quantities of foreign proteins.

Finally, none of these methods is inherently suited to the simultaneous incorporation of adjuvant.

Both the intermediate-release vaccine preparation of this invention and the controlled- or delayed release vaccine preparation are in the form of microspherical particles, preferably in the range of 10 nm to 250 $\mu$m, more preferably in the range of 1 $\mu$m to 100 $\mu$m.

The vaccine preparations in stable particulate form may be made up into vaccine compositions for administration by combining at least one immediate-release vaccine preparation and/or at least one controlled- or delayed-release vaccine preparation with a carrier or diluent acceptable for pharmaceutical or veterinary use. Suitable carriers or diluents for use in the preparation of vaccine compositions for parenteral administration are well known in the art. Alternatively, the vaccine composition may be produced in the form of a solid pellet or implant with known carrier materials.

DETAILED DESCRIPTION OF THE INVENTION

In accordance with the present invention, immunogen-containing microspheres of the controlled- or delayed-release vaccine preparation are produced by a one-step process of manufacture with the potential for a very high throughput. The end-product is a free-flowing powder. As a normal though not essential component of the process, adjuvant is incorporated into these microspheres in association with the immunogen, and this confers a number of advantages:

(i) the immunogen is held in a selected configuration during the drying process, (ii) adjuvant is available to stimulate the immune system at every pulsed release, (iii) during in vivo residence time, whilst delayed-release polymer is undergoing biodegradation, the immunogen is protected from thermal and perhaps enzymic denaturation by attachment to a solid support.

In work leading to the present invention, it has surprisingly been found that an immediate release composition can be provided in stable, solid dry form since it has been generally believed that aluminium salt-adsorbed immunogens could not be prepared in powder or other dry form without recourse to complex technology and excessive and unacceptable use of stabilisers (e.g. Csizer et al.). In accordance with the first aspect of the present invention, however, it has been found that a stable, solid product can be produced as a free-flowing powder by drying an alluminium salt-adsorbed immunogen produced in aqueous suspension. The immunogen may for example be adsorbed on an aluminium salt adjuvant such as aluminium hydroxide or aluminium phosphate. Preferably, the suspension also contains a protein stabiliser, and suitable stabilisers include, for example, sugars and sugar derivatives such as trehalose, lactose, dextrose and glucosamine. The resultant suspension is then dried, preferably spray-dried, to form a free flowing powder. As previously described it has been found that drying of such an aluminium salt-adsorbed immunogen does not denature the immunogen, nor does it degrade the aluminium salt adjuvant, and in fact results from preliminary experiments show that the immunogenicity of the immunogen may be enhanced in such a powder formulation.

In accordance with the second embodiment of the invention, there is provided a process for the manufacture of controlled- or delayed-release microencapsulated vaccines. This process involves the emulsification of vaccine immunogen, preferably in association with adjuvant, all of which comprises the aqueous phase, into a continuous organic phase in which the biodegradable polymer is dissolved. This water-in-oil emulsion is then spray-dried under suitable conditions such as to generate microspheres which comprise a continuous matrix of the polymer surrounding at least one, but preferably many, pockets of immunogen in association with adjuvant.

It will be noted that in accordance with this process, the emulsion which is formed prior to spray drying is a water-in-oil emulsion, in contrast to the oil-in-water emulsions which are produced in the preparation of the delayed-release vaccine compositions of the prior art mentioned above.

In a modification of the process just described, the microspheres may be produced by spray-drying microdroplets which comprise a suspension of micro-particulate immunogen in a solution of the polymer in organic solvent, the micro-particulate antigen being in a form which does not dissolve in the polymer solution, and preferably being the immediate-release vaccine preparation in stable particulate form described herein.

The vaccine preparations of the present invention are applicable for use with a wide variety of immunogens known in both human and veterinary vaccines, including for example tetanus toxoid, diphtheria toxoid, pertussis extract vaccine, influenza virus, and the like.

The biodegradable polymer used in the present invention may be any polymer substance which is capable of existing in a nonaqueous phase, which is biocompatible and which is capable of delayed breakdown in vivo. Suitable polymers include, for example polyesters, polyorthoesters, polyanhydrides and cyanoacrylates, as well as various natural polymers including some proteins and polysaccharides. Particularly suitable polymers for use in accordance with the present invention include homopolymers of D-, L- and DL-polylactic acids (D-PLA; L-PLA; DL-PLA) and polyglycolic acid (PGA), and various copolymers (PLG) thereof. Preferably, in the formation of the water-in-oil emulsion, one or more emulsifiers are used, and suitable emulsifiers include, for example, Tween 80, Span 85 and various lecithins and lecithin-derivatives.

Suitable adjuvants for incorporation into a delayed-release vaccine preparation in accordance with this invention include not only the aluminium salt adjuvants previously described (aluminium hydroxide or aluminium phosphate), but also other particulate and non-particulate adjuvants which are well known in the vaccine field. Suitable adjuvants are described, by way of example, by Cox and Coulter, 1992.

Further features of the vaccine preparations of the present invention and the processes for the preparation thereof will be apparent from the following non-limiting Examples.

EXAMPLE 1

Preparation of an Immediate Release Tetanus Vaccine

*Clostridium tetani* was cultured in a protein-free casein hydrolysate medium for 6 days, at which time approximately 60 Lf/ml (in vitro flocculation units) of tetanus toxin had been produced. Bacterial cells and debris were removed by centrifugation then the toxin concentrated and washed on a 30,000 MW cut-off ultrafiltration membrane. Formaldehyde and lysine solutions were added to a final concentration of 0.3 and 0.9% w/v respectively and toxoiding was allowed to proceed for 2 weeks at 37° C. The resultant toxoid was purified by ammonium sulphate precipitation.

Tetanus toxoid was adsorbed to the aluminium salt adjuvant (aluminium hydroxide or aluminium phosphate) by slow addition of the antigen to the suspension of aluminium adjuvant whilst continuously stirring. The stirring was continued overnight. The aluminium hydroxide gel was sourced as "Alhydrogel" from Superfos, Denmark. The aluminium phosphate gel was prepared by back titration of a solution of aluminium chloride with tri-sodium phosphate. When desired, stabiliser was dissolved in water to a concentration of 50% (w/v) then added to the adsorbed tetanus toxoid to give the required final concentration as stated in Table 1.

The aqueous suspension of aluminium salt-adsorbed tetanus toxoid was spray-dried in a Drytec Compact Laboratory Spray Dryer equipped with a 40/100/120 concentric-type nozzle at an atomising pressure of 80 psi and an outlet temperature of 60° C. The resultant microspheres had a size range around 3 μm in diameter and were collected as a free-flowing powder.

EXAMPLE 2

Preparation of an Immediate-Release Diphtheria Vaccine

*Cornyebacterium diphtheria* was cultured in a medium incorporating casein hydrolysate modified to have a total nitrogen content of 0.2% (w/v) and containing 1.5% (w/v) maltose.

Seed was grown as a 24 hour surface culture in tubes then inoculated into 250 ml volumes in 500 ml Erlenmeyer flasks which were incubated at 35° C. for 3 days on a table rotating at 200 rpm.

Toxin was clarified by filtration to remove bacteria, concentrated to 1% the original volume by ultrafiltration (50,000 MW cut-off) then washed at that volume with half the original volume of PBS. Final purification was on a Sephadex G-100 column, to a purity of 2200 Lf/mg protein nitrogen. The procedure is described in detail by Cox (1975). Formaldehyde and lysine solutions were added to a final concentration of 0.3% and 0.9% (w/v) respectively and toxoiding was allowed to proceed for 4 weeks at 37° C.

Diphtheria toxoid was absorbed to the aluminium salt adjuvant as described previously for tetanus toxoid, and the aqueous suspension of aluminium salt-absorbed diphtheria toxoid was spray-dried as described previously (Example 1).

EXAMPLE 3

Preparation of an Immediate-Release Botulinum C & D Vaccine

*Clostridium botulinum* strains C and D were grown in a cellophane-sac apparatus modified from Sterne (1958). Growth medium external to the sac was a modified corn steep medium which was allowed to equilibrate with PBS within the dialysis sac. Seed cultures of *C. botulinum* were inoculated into the PBS and incubated at 37° C. for 18 days under anaerobic conditions. The contents of the dialysis sac were then harvested, cells removed by centrifugation and formaldehyde to a final concentration of 0.5% (w/v) added. Toxoiding was allowed to occur at 37° C. until complete (7–14 days) then potency was determined as described in the British Pharmacopoeia-Veterinary (1985).

Botulinum toxoids type C and D were mixed with Quil A (Superfos) and spray-dried as described previously for tetanus toxoid (Example 1).

EXAMPLE 4

Preparation of *Bordetella pertussis* Derived PTD Immediate-Release Vaccines

Cultures of *Bordetella pertussis* were grown in shake flasks in a modified Stainer and Sholte medium (Stainer &

Sholte, 1970) containing 1 mg/ml 2,6 di-methylβcyclodextrin. The flasks were incubated at 37° C. with gentle agitation at 180 rpm for 42 hrs when a cell density of around $2.0 \times 10^{10}$ organisms/ml was achieved.

Pertussis toxin (PTX) was purified from the culture supernatant after clarification by filtration. PTX was bound specifically to asialofetuin by affinity chromatography essentially as described by Sekura et al. (1985), washed, then eluted with 50 mM Tris/4M urea buffer, pH 9.0.

PTX was toxoided at pH 9.6 in the presence of 2.5 mM glutaraldehyde for 48 hrs at 4° C. when reaction was terminated by addition of 9 mM lysine. The method was essentially as described in Australian Patent Specification No. 601415 (71581/87). The resultant pertussis toxoid (PTD) was adsorbed to the aluminium salt adjuvant and spray-dried as described previously.

EXAMPLE 5

Preparation of Delayed-Release Tetanus Vaccine
A. Emulsion Procedure

50:50 and 85:15 copolymers of polylactide and polyglycolide (PLG) and the homopolymer of polylactic acid (PLA) were obtained from Birmingham Polymers Ltd., Birmingham, Ala., U.S.A. The copolymers were solubilised to 10% w/v dissolution in either chloroform or a mix of 5 parts of trichloroethylene and 3 parts of 1,1,2-trichloroethane. For each of these polymer solutions, an emulsion was produced as follows:

(a) to 93 parts of polymer solution were added 1 part of soya lecithin and 6 parts of an aqueous suspension of aluminium salt-adsorbed tetanus toxoid, or (b) to 88 parts of polymer solution were added 1 part of a 1:5 mixture of TWEEN 80 and SPAN 85 and 11 parts of an aqueous suspension of aluminium salt-absorbed tetanus toxoid.

The production of the aqueous suspension of aluminium salt-adsorbed tetanus toxoid is described in Example 1 above. The mixture was vigorously agitated using either an ultrasonic probe or a high-speed blender (e.g. a Silverson blender) to produce a stable water-in-oil emulsion with a milk-like consistency and appearance. This emulsion was spray-dried using a Drytec Compact Laboratory Spray Dryer equipped with a 40/100/120 concentric-type nozzle at an atomising pressure of 30 psi and an outlet temperature of 35° C. The resultant microspheres had a size range around 30 μm in diameter and were collected as a free-flowing powder. Traces of remaining organic solvent were removed by vacuum evaporation. A number of preparations were made to permit consideration of the following variables:

(a) choice of polymer—50:50 PLG 85:15 PLG PLA
(b) choice of adjuvant—aluminium hydroxide—aluminium phosphate
(c) choice of stabiliser—0, 0.5 and 5.0% trehalose.

B. Suspension Procedure

Polymer solutions were prepared as described in Section A above, then microspheres of particulate immediate-release aluminium salt-adsorbed tetanus toxoid, prepared as described in Example 1, were added to a final 1% w/v suspension. The mixture was agitated sufficiently to maintain an even suspension and spray-dried as described in Section A above to a particle size around 30 μm. In some experiments, tetanus toxoid, spray-dried to small microspheres but in the absence of any aluminium salt adjuvant, was suspended similarly in polymer solution, and larger microspheres spray-dried as described.

EXAMPLE 6

Preparation of Delayed-Release Botulinum C & D Vaccines by Emulsion Procedure

50:50 and 85:15 copolymers of PLG and the homopolymer PLA were solubilised to 10% w/v in dichloromethane. For each of these polymer solutions, a water-in-oil type emulsion was made as follows: to 88 parts polymer solution was added 1 part of a 1:5 mixture of Tween 80 and Span 85 and 11 parts of an aqueous mixture of botulinum C and D toxoids and Quil A. The mixture was vigorously agitated using a high-speed blender then immediately spray-dried using a Drytec Compact Laboratory Spray Dryer equipped with a 60/100/120 nozzle at an atomising pressure of 15 psi and an inlet temperature of 65° C. The resultant microspheres had a size range of around 20 μm diameter and were collected as a free-flowing powder. Traces of remaining organic solvent were removed by vacuum evaporation.

EXAMPLE 7

Incorporation of Microspheres into Implants

The microspherical particles of the present invention may be formed into implants, particularly for implantation into subcutaneous tissues of livestock and companion animals. This method has the advantage of delivering a large number of microspheres in a simple, easily packaged device. The implants may contain "immediate" release microspheres, "delayed release microspheres" or a defined mixture of both delayed and immediate release microspheres to give the desired release for a particular vaccine or active immunogen. These implants are usually cylindrical in shape and produced by standard pharmaceutical tabletting procedures. Various excipients may be added to aid in the compression and tabletting processes such as calcium phosphate, Emcompress®, lactose, dextrose, lysine and magnesium stearate. Other excipients such as a disintegrant (e.g. sodium starch glycolate; Explotab®) may also be added to increase the dispersion characteristics of the microspheres upon implantation. The size of the implants may be varied depending on the amount of microspheres required per dose, but would normally be in the range of 2–4 mm in diameter and 3–10 mm long. Further polymer coatings may be applied to the implants to accelerate or retard the release of the active immunogen following implantation.

EXAMPLE 8

A. Testing of Vaccine Preparations
(a) In vitro testing

Aluminium phosphate gel was solubilised by dilution to 2 mg $AlPO_4$/ml in saline containing a final concentration of 10% w/v sodium citrate. Samples were incubated at 37° C. overnight or until completely clear. This treatment yielded an aqueous solution in which previously bound protein molecules were freed for assay as described below.

Tetanus prototoxin

Purified tetanus prototoxin was produced by exaction from cells of *Clostridium tetani* harvested prior to commencement of autolysis. Preferably, cells were harvested 72 to 90 hr after inoculation and immediately chilled at 4° C. and held at that temperature during subsequent processing. The culture was centrifuged at 10,000 g for 25 min, washed twice in 0.15M NaCl then resuspended to 1/30 the original volume in 1M NaCl, 0.1M sodium citrate pH 7.5 containing 1 mM phenylmethysulphonyl chloride (PMSF), 1 mg/ml pepstatin and 1 mg/ml leupeptin. After 16 h, extracted prototoxin was separated from cell debris by centrifugation.

Initial prototoxin purification was by precipitation and washing with 40% saturated ammonium sulphate, followed by resuspension in 0.1M phosphate buffer pH6.8 containing 1 mM PMSF and 1 mg/ml each of pepstatin and leupeptin. Final purification was performed in this buffer on an anion exchange column of an FPLC.

Diphtheria toxin

Purified diphtheria toxin as described in Example 2 with a purity of 2200 Lf/mg protein nitrogen.

Botulinum C and D toxin

Botulinum toxins were clarified by filtration then concentrated and partially purified by ultrafiltration (50,000 MW cut-off).

B. pertussis PTX

PTX was purified as described in Example 4. Final purity was in excess of 99%.

Enzyme immunoassay

Purified antigen was diluted to 10 μg/ml (approx 5 Lf/ml) in 0.05M sodium bicarbonate buffer pH 9.6 and used to coat polystyrene plates (Maxisorb/NUNC, Denmark) overnight at 4° C. At the end of this incubation, contents were aspirated and the wells post-coated with casein solution (1 mg/ml) in 0.01M phosphate buffered saline (PBS) pH 7.2 for 1 hr at 20° C. Contents were again discarded, the wells were rinsed with stabilising solution then plates were dried and stored in sealed metal foil pouches.

All serum dilutions were performed in Blue Diluent (CSL, Australia) a PBS Tween diluent containing casein. Test samples were incubated for 60 min at 20° C. (0.1 ml/well), washed 6 times with PBS Tween then incubated similarly with horse radish peroxidase (HRP)-conjugated sheep anti-mouse Ig, sheep anti-horse Ig, or rabbit anti-sheep Ig. Peroxidase activity was measured by addition of 0.1 ml/well of substrate solution containing $H_2O_2$ and tetramethyl benzidine. After 5 min at room temperature, the reaction was stopped by addition of 0.05 ml/well 0.5M $H_2SO_4$. Absorbance readings were made at 450 nm on an automated EIA plate reader. Titration of a subsidiary standard serum of 115 IU/ml was included on all plates.

(b) In vivo testing

Naive mice were dosed subcutaneously with a total of 0.1 to 1.0 Lf tetanus toxoid and 1 μg of each of diphtheria toxoid and PTD. Mice were eyebled at regular intervals and their serum antibody levels tested by EIA using the above described validated assay.

Sheep were dosed with bivalent botulinum which contained 2 cpu/dose botulinum C toxoid, 21.8 cpu/dose botulinum D toxoid and 0.4 mg Quil A.

Horses were dosed with 10 Lf/dose of tetanus toxoid by the intramuscular route.

B. Results for immediate release preparations

Table 1 shows in vitro and in vivo testing data for a range of microspherical immediate-release vaccine preparations produced in accordance with Example 1. Group 7 was the positive control; titres of 100 are considered background. It can be seen that inclusion of 5% trehalose along with tetanus toxoid adsorbed to either aluminium hydroxide or phosphate permitted the formation of microspheres with a high retention of in vitro activity and no reduction in immunogenicity (Group 2 and 6).

TABLE 1

| GROUP | DOSE | MEDIAN TITRE | % EIA Activity |
|---|---|---|---|
| 1 | TT-AlPO$_4$ s/d | 100 | 3.9 |
| 2 | TT-AlPO$_4$ + 5% trehalose | 1500 | 70.2 |
| 3 | TT-AlPO$_4$ + 5% glucosamine | 1150 | 74.3 |
| 4 | TT-AlPO$_4$ + 5% lactose | 900 | 74.4 |

TABLE 1-continued

| GROUP | DOSE | MEDIAN TITRE | % EIA Activity |
|---|---|---|---|
| 5 | TT-Al(OH)$_3$ s/d | 100 | N.T. |
| 6 | TT-Al(OH)$_3$ + 5% trehalose | 1550 | N.T. |
| 7 | TT-AlPO$_4$ suspension | 1540 | 100 |
| 8 | TT-Al(OH)$_3$ suspension | 1600 | N.T. |
| 9 | TT s/d | 100 | 67.0 |

Table 2 shows in vivo testing data in mice for microspherical immediate-release diphtheria-toxoid (DT) and B. pertussis PTD vaccines. It can be seen that in all cases, the dried microparticulate vaccine was at least as immunogenic as the liquid vaccine from which it was produced when given at the same dose level based on the assumption of zero losses during drying.

TABLE 2

| | | Median antibody titre (week) | | | | | |
|---|---|---|---|---|---|---|---|
| Group | Vaccine | 2 | 4 | 8 | 12 | 16 | 20 |
| | DT-AlPO$_4$ | | | | | | |
| 1 | dried | 1600 | 850 | 700 | 530 | 500 | 200 |
| 2 | liquid | 500 | NT | 500 | 240 | 190 | 130 |
| | PTD-AlPO$_4$ | | | | | | |
| 3 | dried | 150 | 430 | 190 | 45 | 60 | 40 |
| 4 | liquid | 40 | 190 | NT | NT | 52 | 36 |

NT = not tested

Table 3 shows in vivo testing data in horses for microspherical immediate release tetanus vaccine. Results show secondary titres 4 weeks after the second dose (doses were given at 4 wk intervals). All horses were seronegative 4 weeks after primary immunisation. It can be seen that horses that were boosted with the dried vaccine (horses 1, 2 and 7) have titres on average which are better than the horse that received the liquid vaccine boost (horse 8).

TABLE 3

| | | Titre | |
|---|---|---|---|
| Number | Dose (secondary) | 4 week | 8 week |
| 1 | Dried immediate release | ND | 500 |
| 2 | " | ND | 7500 |
| 3 | 85:15 delayed release* | ND | 100 |
| 4 | " | ND | 500 |
| 5 | " | ND | 400 |
| 6 | " | ND | 400 |
| 7 | Dried immediate release | ND | 12500 |
| 8 | Liquid vaccine | ND | 1000 |
| 9 | none | ND | ND |
| 10 | none | ND | ND |

ND = not detectable.
* Delayed-release component given in combination with primary dose.

Table 4 shows in vivo testing data in sheep for microspherical immediate release botulinum C & D vaccine adjuvanted with Quil A. Five animals were dosed per group. It can be seen that 2 doses of dried immediate-release vaccine has given identical results to 2 doses of normal liquid vaccine over a 12 week examination period (group 2 of group 1).

TABLE 4

| Number | Dose 1° | 2° | Antibody titre (units) Wk 4 | 8 | 12 |
|---|---|---|---|---|---|
| 1 | liquid | liquid | 1.3 | 14.3 | 3.4 |
| 2 | dry immed. release | dry immed. release | 2.0 | 12.0 | 4.4 |
| 3 | 50:50 delay release | " | 12.2 | 3.9 | 1.3 |
| 4 | 85:15 delay release | " | 5.8 | 2.1 | 3.6 |
| 5 | dry immed. release + 50:50 delay release | " | 7.2 | 2.3 | 1.0 |
| 6 | dry immed. release + 85:15 delay release | " | 6.9 | 8.3 | 1.7 |

C. Results for delayed-release preparations

Table 5 shows the in vivo testing for a range of microspherical, delayed-release vaccines. All mice were dosed with 1 Lf tetanus toxoid except group 1 which are the negative controls. Group 2 is the positive control (liquid aluminium adsorbed tetanus toxoid) and group 3 is unadsorbed antigen. Groups 4 to 7 were prepared by the suspension procedure, groups 8 to 13 by the emulsion procedure. Substantial delayed release responses can be seen, especially for groups 9, 11 and 13.

TABLE 5

| Group No. | VACCINE | MEDIAN Ab TITRE 2 Wks | 4 Wks | 8 Wks |
|---|---|---|---|---|
| 1 | no treatment | 100 | 100 | 100 |
| 2 | TT-AlPhos susp | 2250 | 4200 | 5950 |
| 3 | soluble TT | 350 | 300 | 400 |
| 4 | 50:50 PLG s/d TT | 850 | 700 | 2500 |
| 5 | 50:50 PLG s/d TT-AlPhos | 700 | 500 | 3950 |
| 6 | 85:15 PLG s/d TT | 700 | 1350 | 1700 |
| 7 | 85:15 PLG s/d TT AlPhos | 1450 | 1050 | 2700 |
| 8 | 50:50 PLG liq TT | 900 | 1000 | 2950 |
| 9 | 50:50 PLG liq TT-AlPhos | 700 | 1450 | 6300 |
| 10 | 85:15 PLG liq TT | 550 | 550 | 1750 |
| 11 | 85:15 PLG liq TT-AlPhos | 500 | 700 | 6900 |
| 12 | 100% PLA liq TT | 550 | 450 | 4300 |
| 13 | 100% PLA liq TT-AlPhos | 600 | 450 | 5350 | s/d = spray-dried
TT = tetanus toxoid

Table 6 shows the in vivo testing for a range of microspherical delayed-release vaccines. These vaccines were prepared using trehalose (5% w/v) as antigen stabiliser and mice were dosed with 0.1 Lf tetanus toxoid per dose. All vaccines were given as a single dose and bleeds taken for assay at the specified time. The results show significant delayed release responses for all the delayed-release vaccines as compared with an erosion in response for groups which received immediate-release vaccine only, either liquid or dried (groups 1 to 3).

TABLE 6

| GP No. | Vaccine | Nozzle | Median EIA Titre 2 wks | 4 wks | 8 wks | 12 wks |
|---|---|---|---|---|---|---|
| 1 | TT-AlPO$_4$ suspension | | 100 | 100 | 100 | 100 |
| 2 | TT-AlPO$_4$ spray dried | 40/100/120 | 200 | 200 | 300 | 200 |
| 3 | TT-AlPO$_4$ spray dried | 60/100/120 | 250 | 200 | 150 | 100 |
| 4 | no treatment | | 100 | 100 | 100 | 100 |
| 5 | TT-AlPO$_4$ in 50:50 PLG | 40/100/120 | 750 | 1200 | 6750 | 1100 |
| 6 | TT-AlPO$_4$ in 50:50 PLG | 60/100/120 | 500 | 500 | 4650 | 450 |
| 7 | TT-AlPO$_4$ in 85:15 PLG | 40/100/120 | 500 | 700 | 2200 | 1650 |
| 8 | TT-AlPO$_4$ in 85:15 PLG | 60/100/120 | 550 | 600 | 2250 | 2400 |
| 9 | TT-AlPO$_4$ in 100% PLA | 40/100/120 | 500 | 800 | 900 | 600 |
| 10 | TT-AlPO$_4$ in 100% PLA | 60/100/120 | 350 | 800 | 1700 | 2100 |

Note:
all preparations contain 5% trehalose.

Table 3 shows the results of tetanus toxoid vaccines in horses. It can be seen that a single dose of immediate-release vaccine (horses 9 and 10) failed to induce detectable antibody levels in horses over the 8 week study period. Conversely, horses which received a single dose of vaccine which contained both immediate and delayed-release components (horses 3 to 6) showed definite antibody titres at week 8 as a result of the delayed release. Titers at 8 weeks were not as high as for horses receiving 2 doses of vaccine, but it is expected that titres will persist longer.

Table 4 shows the results of botulinum C and D vaccination of sheep. It can be seen that the single dose delayed-release vaccines both on their own (groups 3 and 4) and in combination with immediate release vaccine have given titers at 12 weeks comparable to two doses of immediate-release vaccine and well in excess of that expected from a single dose of immediate release vaccine. It is of further significance that this result was obtained using Quil A as the adjuvant.

EXAMPLE 9

Preparation of Controlled-Release Vaccine by the Suspension Route Using Spray-Drying This method was used with small samples of toxoid suspensions, typically 0.6 to 1 gm in 10 ml or 1.6 to 2 gm in 60 ml, which could not be processed in a standard spray dryer. A special spray dryer able to process such small quantities was set up which atomised the slurry using a piezoelectrically powered ultrasonic nozzle, (Sono-Tek Corp. Model 8700-120MS). The advantage of this nozzle is that it is able to create small droplets without the use of large volumes of a second fluid or the use of high pressure which requires much space and surface making a small amount of material difficult to collect. The unit was provided with a source of hot air, cold air and a filter. The hot air carried the atomised spray allowing the water to evaporate. Cold air was then mixed with the hot air before collecting the dried sample on a filter. The bottom of the 11 cm diameter filter was connected to a source of vacuum. There were 3 thermocouples in the device, one at the top near the nozzle, one in the middle of the device and one at the filter.

Two types of samples were processed, (1) a "saturated" preparation of 30,000 Lf tetanus toxoid adsorbed on AlPO$_4$, each bottle containing 0.6 g AlPO$_4$ in 12 ml of pyrogen free water and (2) a "saturated/3" preparation of 30,000 Lf tetanus toxoid adsorbed on 1.65 g AlPO$_4$ in 60 ml of pyrogen free water. Both samples were sterile. Feed rate of the slurry which was added under agitation conditions was between 1 and 3 ml/min. The power to the nozzle which operated at 120 khz was about 7 watt. The filter was set to 6 in mercury of vacuum and the cold air at 500 cm$^3$/min. Typical thermocouple readings were 63 to 86° C. at the top near the nozzle, 83 to 85° C. in the middle and 46 to 58° C. at the bottom near the collection filter.

Micrographs of the product showed 5 to 20 micron spheres for the more dilute samples and 10 to 30 micron for the more concentrated samples. Solid recovery ranged from 40 to 70%.

The product from the "saturated" samples was divided into 3 portions each being 0.865 g solids. Three solutions were prepared each 20 gm polymer in 200 ml of solvent. Poly(DL-lactide) (inherent viscosity 0.73 at 0.5 g/dl) and 85/15 Poly(DL-lactide-co-glycolide) (inherent viscosity 0.65 at 0.5 g/dl) were dissolved in trichloroethylene 5 parts, 3 parts 1,1,2-trichloroethane, whereas 50/50 Poly(DL-lactide-co-glycolide) (inherent viscosity 0.71 at 0.5 g/dl) was dissolved in chloroform 5 parts, 3 parts 1,1,2-trichloroethane. The solids were dispersed in the solution and stirred for 30 minutes before being sprayed with a two-fluid nozzle (Spraying Systems, fluid cap 40100, air cap 120) at 20 psi. It was sprayed into room temperature air and after drying recovered on cloth filters. The particles were separated on a 104 micron sieve.

The product from the "saturated/3" samples was treated essentially the same way, except in this case 1.5 gm sample was available for each final spray run, therefore the ratio of toxoid solids to polymer was 1.5 to 20 in this case instead of 0.965 to 20 for the "saturated" case.

EXAMPLE 10

Preparation of Polylactide Encapsulated Toxoid by the Spray-Dried Emulsion Technique 20 g of Poly(DL-lactide) supplied by Birmingham Polymers, Inc. (inherent viscosity 0.73 g/dl) was dissolved in a mixture of 105 ml of trichloroethylene and 70 ml toluene by stirring overnight with a magnetic spin bar. Sodium dioctyl sulfosuccinate also known as sodium docusate (2.0 gm) was added with stirring until dissolution was complete. The saturated aqueous suspension of aluminium salt-adsorbed tetanus toxoid (12 ml) was added in a thin stream to the polymer solution which was stirred with a spin bar. Also, an ultrasonic probe was included to provide the necessary shear for stable emulsion preparation with this small volume of solution. The mixture was fed by syringe to a 2-fluid spray nozzle contained in a spray drying chamber at approximately 30 ml/min. The inlet temperature to the spray chamber was at ambient and nozzle pressure was controlled at 20 psi. The product after drying was removed from the outlet filter socks.

REFERENCES

1. Cox, J. C. and Coulter, A. R. (1992), "Advances in adjuvant technology and application" in *Animal Parasite Control Utilising Biotechnology*, ed. W. K. Yong, CRC Press Inc., Boca Raton, Fla., pp49–112.
2. Eldridge, J. H., Hammond, C. J., Meulbroek, J. A., Staas, J. K., Gilley, R. M. and Tice, T. R. Controlled vaccine release in the gut-associated lymphoid tissues. I. Orally administered biodegradable microspheres target the Peyer's patches, *J.Control. Release*, 11, 205, 1990.
3. Eldridge, J. H., Staas, J. K., Meulbroek, J. A., McGhee, J. R., Tice, T. R. and Gilley, R. M. Biodegradable microspheres as a vaccine delivery system. *Mol. Immunol.* 28, 287, 1991.
4. Kreuter, J. Large-scale production problems and manufacturing of nanoparticles, in *Specialized Drug Delivery Systems. Manufacturing and Production Technology.* Tyle, P., Ed., Marcel Dekker, New York, 1990, 257.
5. O'Hagan, D. T., Jeffery, H., Roberts, M. J. J., McGee, J. P. and Davis, S. S. Controlled release microparticles for vaccine development. *Vaccine* 9, 768, 1991.
6. Singh, M., Singh, A. and Talwar, G. P. Controlled delivery of diphtheria toxoid using biodegradable poly(D,L-lactide) microcapsules. *Pharm. Res.* 8, 958, 1991.
7. Bodmeier, R. and Cheng, H. Preparation of biodegradable poly(±)lactide microparticles using a spray-drying technique. *J.Pharm.Pharmacol,* 40, 754, 1988.
8. Cox, J. New methods for the large-scale preparation of diphtheria toxoid: Purification of toxin. *App. Microbiol.* 29, 464, 1975.
9. Sterne, M. The growth of *Brucella abortus* strain 19 in aerated dialysed medium. *J. Gen. Micro.* 18, 747, 1958.
10. British Pharmacopoeia-Veterinary (1985). Her Majesty's Stationery Office, London.
11. Stainer, D. and Sholte, M. A simple chemically defined medium for the production of Phase I *Bordetella pertussis. J. Gen. Micro.* 63, 211, 1970.
12. Sekura, R. D., Zhang, Y. I. and Quentin-Millet, M.-J. B. Pertussis toxin: Structural elements involved in the interaction with cells. Pertussis toxin. Ed. Sekura et al., Academic Press, p.45, 1985.

We claim:

1. A vaccine preparation in stable, dry particulate form, comprising microspherical particles prepared by spray-drying, said particles comprising an immunogen adsorbed to an aluminum salt adjuvant, said vaccine preparation being a free flowing powder.

2. The vaccine preparation of claim 1, wherein said aluminium salt adjuvant is aluminium hydroxide or aluminium phosphate.

3. The vaccine preparation of claim 1 further comprising a protein stabiliser.

4. The vaccine preparation of claim 3, wherein said stabiliser is a sugar or sugar derivative.

5. The vaccine preparation of claim 4 wherein said stabiliser is selected from the group consisting of trehalose, lactose, dextrose and glucosamine.

6. A method for the production of a vaccine preparation of claim 1, which comprises the steps of forming an aqueous suspension of aluminium salt-adsorbed immunogen, and subsequently spray-drying said suspension.

7. A vaccine composition comprising at least one vaccine preparation of claim 1, together with a pharmaceutically or veterinarily acceptable carrier or diluent.

8. The vaccine composition of claim 7 wherein the carrier or diluent is suitable for parenteral administration.

9. The vaccine composition of claim 7, wherein said carrier is a solid carrier and said vaccine composition is in the form of a solid pellet or implant.

10. A method of vaccinating a human or other animal patient, which comprises administration to the patient of a vaccine composition of claim 7.

11. A vaccine preparation in stable, dry particulate form, comprising microspherical particles prepared by spray-drying said particles comprising a continuous matrix of biodegradable polymer containing one or more discrete, immunogen-containing regions, said vaccine preparation being a free flowing powder.

12. The vaccine preparation of claim 11, wherein said immunogen-containing regions also contain an adjuvant.

13. The vaccine preparation of claim 11, wherein said immunogen-containing regions contain particles comprising an immunogen adsorbed to an aluminium salt adjuvant.

14. The vaccine preparation of claim 11, wherein said biodegradable polymer is selected from the group consisting of polylactic acid, polyglycolic acid, and copolymers thereof.

15. A method for the production of a vaccine preparation of claim 11, which comprises the steps of forming an emulsion of an aqueous suspension comprising immunogen and optionally an adjuvant in a continuous organic phase having biodegradable polymer dissolved therein, and subsequently spray-drying the water-in-oil emulsion to form microspherical particles.

16. The method of claim 15, wherein said emulsion includes an emulsifier.

17. The method of claim 15, wherein the immunogen is adsorbed to an aluminium salt adjuvant.

18. A method for the production of a vaccine preparation of claim 11, which comprises the steps of forming a suspension of a particulate immunogen-containing material and optionally an adjuvant in a continuous organic phase having biodegradable polymer dissolved therein, and subsequently spray-drying the suspension to form microspherical particles.

19. The method of claim 18, wherein the particulate immunogen-containing material comprises an immunogen adsorbed to an aluminium salt adjuvant.

20. A vaccine composition comprising at least one vaccine preparation of claim 11, together with a pharmaceutically or veterinarily acceptable carrier or diluent.

21. The vaccine composition of claim 20 further comprising at least one vaccine preparation in stable, dry particulate form, comprising microspherical particles prepared by spray-drying, said particles comprising an immunogen adsorbed to an aluminum salt adjuvant, said vaccine preparation being a free flowing powder.

22. The vaccine composition of claim 21, wherein said vaccine preparation comprises an immunogen adsorbed to an aluminium salt adjuvant.

23. The vaccine composition of claim 20, wherein the carrier or diluent is suitable for parenteral administration.

24. The vaccine composition of claim 20, wherein said carrier is a solid carrier and said vaccine composition is in the form of a solid pellet or implant.

25. A method of vaccinating a human or animal patient, which comprises administration to the patient a vaccine composition of claim 20.

26. A vaccine preparation in stable, dry particulate form comprising microspherical particles prepared by spray drying an emulsion of an aqueous suspension comprising immunogen in a continuous organic phase having biodegradable polymer dissolved therein or by spray drying a suspension of particulate immunogen-containing material in a continuous organic phase having biogradable polymer dissolved therein, said vaccine preparation being a free flowing powder.

* * * * *